(12) United States Patent
Grill, Jr. et al.

(10) Patent No.: US 10,086,204 B2
(45) Date of Patent: Oct. 2, 2018

(54) NON-REGULAR ELECTRICAL STIMULATION PATTERNS FOR TREATING NEUROLOGICAL DISORDERS

(71) Applicant: Duke University, Durham, NC (US)

(72) Inventors: Warren M. Grill, Jr., Chapel Hill, NC (US); Alan D. Dorval, II, Salt Lake City, UT (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 14/542,785

(22) Filed: Nov. 17, 2014

(65) Prior Publication Data
US 2015/0073495 A1    Mar. 12, 2015

Related U.S. Application Data

(63) Continuation of application No. 13/897,504, filed on May 20, 2013, now Pat. No. 9,259,579, which is a
(Continued)

(51) Int. Cl.
*A61N 1/36* (2006.01)
*A61N 1/372* (2006.01)
*A61N 1/05* (2006.01)

(52) U.S. Cl.
CPC .......... *A61N 1/36178* (2013.01); *A61N 1/36* (2013.01); *A61N 1/3615* (2013.01); *A61N 1/36064* (2013.01); *A61N 1/36067* (2013.01); *A61N 1/36071* (2013.01); *A61N 1/36082* (2013.01); *A61N 1/36096* (2013.01); *A61N 1/36171* (2013.01); *A61N 1/37235* (2013.01); *A61N 1/0534* (2013.01); *A61N 1/36196* (2013.01)

(58) Field of Classification Search
CPC ............ A61N 1/36014; A61N 1/36021; A61N 1/3605; A61N 1/36089; A61N 1/36096; A61N 1/36064; A61N 1/36067
USPC ............................ 607/45, 66, 68, 70, 72, 73
See application file for complete search history.

(56) References Cited

U.S. PATENT DOCUMENTS

| | | |
|---|---|---|
| 3,833,005 A | 9/1974 | Wingrove |
| 4,338,945 A | 7/1982 | Kosugi et al. |

(Continued)

FOREIGN PATENT DOCUMENTS

| | | |
|---|---|---|
| EP | 1145735 | 10/2001 |
| WO | WO2010/039274 | 4/2010 |

OTHER PUBLICATIONS

International Search Report and the Written Opinion of the International Searching Authority, PCT/US2013/046183, Duke University, dated Oct. 4, 2013.
(Continued)

*Primary Examiner* — Paula J Stice
(74) *Attorney, Agent, or Firm* — McDonald Hopkins LLC

(57) ABSTRACT

Systems and methods for stimulation of neurological tissue generate stimulation trains with temporal patterns of stimulation, in which the interval between electrical pulses (the inter-pulse intervals) changes or varies over time. Compared to conventional continuous, high rate pulse trains having regular (i.e., constant) inter-pulse intervals, the non-regular (i.e., not constant) pulse patterns or trains that embody features of the invention provide a lower average frequency.

28 Claims, 8 Drawing Sheets

Related U.S. Application Data continuation of application No. 12/587,295, filed on Oct. 5, 2009, now Pat. No. 8,447,405.

(60) Provisional application No. 61/102,575, filed on Oct. 3, 2008.

(56) References Cited

U.S. PATENT DOCUMENTS

| | | | |
|---|---|---|---|
| 5,018,524 A | 5/1991 | Gu et al. | |
| 5,095,904 A | 3/1992 | Seligman et al. | |
| 5,485,851 A * | 1/1996 | Erickson | 600/529 |
| 5,716,377 A | 2/1998 | Rise et al. | |
| 6,560,487 B1 * | 5/2003 | McGraw et al. | 607/51 |
| 6,560,490 B2 | 5/2003 | Grill et al. | |
| 6,944,501 B1 | 9/2005 | Pless | |
| 7,010,351 B2 | 3/2006 | Firlik et al. | |
| 7,191,014 B2 | 3/2007 | Kobayashi et al. | |
| 8,073,544 B2 | 12/2011 | Pless | |
| 8,355,789 B2 * | 1/2013 | Werder et al. | 607/45 |
| 8,447,405 B2 | 5/2013 | Grill et al. | |
| 2002/0177882 A1 | 11/2002 | DiLorenzo | |
| 2003/0135248 A1 | 7/2003 | Stypulkowski | |
| 2004/0158298 A1 | 8/2004 | Gliner et al. | |
| 2004/0249422 A1 | 12/2004 | Gliner et al. | |
| 2005/0060009 A1 | 3/2005 | Goetz | |
| 2005/0222641 A1 | 10/2005 | Pless | |
| 2006/0015153 A1 | 1/2006 | Gliner et al. | |
| 2006/0212089 A1 * | 9/2006 | Tass | A61N 1/36017 607/45 |
| 2007/0288064 A1 | 12/2007 | Butson et al. | |
| 2009/0131993 A1 | 5/2009 | Rousso et al. | |
| 2010/0121416 A1 | 5/2010 | Lee | |
| 2010/0152807 A1 | 6/2010 | Grill et al. | |
| 2011/0093041 A1 | 4/2011 | Straka et al. | |

OTHER PUBLICATIONS

International Search Report and the Written Opinion of the International Searching Authority, PCT/US2012/059787, Duke University, dated Jan. 4, 2013.

International Preliminary Examination Report, PCT/US2009/05459, Duke University, dated Jan. 11, 2011.

International Search Report and the Written Opinion of the International Searching Authority, PCT/US2009/05459, Duke University, dated Dec. 3, 2009.

Extended European Search Report, Application No. 09818122.5-1652/2340078, Duke University, dated Aug. 2, 2013.

Rubin, Jonathan et al., High Frequency Stimulation of the Subthalamic Nucleus Eliminates Pathological Thalamic Rhythmicity in a Computational Model, Journal of Computational Neuroscience, vol. 16, pp. 211-235, 2004.

McIntyre, Cameron et al., Cellular Effects of Deep Brain Stimulation: Model-Based Analysis of Activation and Inhibition, J. Neurophysiol, vol. 91, pp. 1457-1469, 2004.

Birdno, Merrill Jay, Analyzing the Mechanisms of Action of Thalamic Deep Brain Stimulation: Computational and Clinical Studies, Ph. D. Dissertation, Department of Biomedical Engineering, Duke University, Durham, NC, USA, Aug. 2009.

Constantoyannis, Constantine, et al., Tremor Induced by Thalamic Deep Brain Stimulation in Patients with Complex Regional Facial Pain, Movement Disorders, vol. 19, No. 8, pp. 933-936, 2004.

Benabid, Alim et al., Long-term suppression of tremor by chronic stimulation of the ventral intermediate thalamic nucleus, The Lancet, vol. 337, pp. 403-406, Feb. 16, 1991.

Davis, Lawrence, Handbook of Genetic Algorithms, Van Nostrand Reinhold, NY, pp. 1-402, 1991.

Dorval, Alan et al., Deep Brain Stimulation Alleviates Parkinsonian Bradykinesia by Regularizing Pallidal Activity, J. Neurophysiol, vol. 104, pp. 911-921, 2010.

Fogelson, Noa et al., Frequency dependent effects of subthalamic nucleus stimulation in Parkinson's disease, Neuroscience Letters 382, 5-9, 2005.

Grefenstette, John, Optimization of Control Parameters for Genetic Algorithms, IEEE Transactions on Systems, Man, and Cybernetics, vol. SMC-16, No. 1, pp. 122-128, Jan./Feb. 1986.

Feng, Xiao-jiang et al., Optimal Deep Brain Stimulation of the Subthalamic Nucleus—a Computational Study, Journal of Computational Neuroscience, 23(3):165-282, Jan. 9, 2007.

Grill, W.M. et al., Effect of waveform on tremor suppression and paresthesias evoked by thalamic deep brain stimulation (dbs), Society for Neuroscience Abstract 29, 2003.

Kuncel, Alexis et al., Clinical Response to Varying the Stimulus Parameters in Deep Brain Stimulation for Essential Tremor, Movement Disorders, vol. 21, No. 11, pp. 1920-1928, 2006.

Kupsch, A. et al., The effects of frequency in pallidal deep brain stimulation for primary dystonia, J. Neurol 250:1201-1205, 2003.

Tinnerman, Lars et al., The cerebral oscillatory network of parkinsonian resting tremor, Brain, 126, pp. 199-212, 2003.

Limousin, Patricia et al., Effect on parkinsonian signs and symptoms of bilateral subthalamic nucleus stimulation, The Lancet, vol. 345, pp. 91-95, Jan. 14, 1995.

Brocker, David. et al., Improved Efficacy of Temporally Non-Regular Deep Brain Stimulation in Parkinson's Disease, Department of Biomedical Engineering, Duke University, Durham NC 27708-0281, pp. 1-34.

Extended European Search Report, Application No. 13875748.9-1666/2874692, Duke University, dated Mar. 9, 2016.

* cited by examiner

NON-REGULAR ELECTRICAL STIMULATION PATTERNS FOR TREATING NEUROLOGICAL DISORDERS

CROSS-REFERENCE TO RELATED APPLICATION

This application is a continuation of co-pending U.S. patent application Ser. No. 13/897,504, filed May 20, 2013, and entitled "Non-Regular Electrical Stimulation Patterns for Treating Neurological Disorders," which is a continuation of U.S. patent application Ser. No. 12/587,295, now U.S. Pat. No. 8,447,405, filed Oct. 5, 2009, and entitled "Non-Regular Electrical Stimulation Patterns for Treating Neurological Disorders," which claimed the benefit of U.S. Provisional Patent Application Ser. No. 61/102,575, filed Oct. 3, 2008, and entitled "Stimulation Patterns For Treating Neurological Disorders Via Deep Brain Stimulation," which are both incorporated herein by reference.

FIELD OF THE INVENTION

This invention relates to systems and methods for stimulating nerves in animals, including humans.

BACKGROUND OF THE INVENTION

Deep Brain Stimulation (DBS) has been found to be successful in treating a variety of brain-controlled disorders, including movement disorders. Generally, such treatment involves placement of a DBS type lead into a targeted region of the brain through a burr hole drilled in the patient's skull, and the application of appropriate stimulation through the lead to the targeted region.

Presently, in DBS, beneficial (symptom-relieving) effects are observed primarily at high stimulation frequencies above 100 Hz that are delivered in stimulation patterns or trains in which the interval between electrical pulses (the inter-pulse intervals) is constant over time. The trace of a conventional stimulation train for DBS is shown in FIG. 2. The beneficial effects of DBS on motor symptoms are only observed at high frequencies, while low frequency stimulation may exacerbate symptoms See Benabid et al. 1991, Limousin et al. 1995. Thalamic DBS at less than or equal to 50 Hz increases tremor in patients with essential tremor. See Kuncel et al. 2006. Similarly, 50 Hz DBS produces tremor in pain patients receiving simulation of the ventral posterior medial nucleus of the thalamus (VPM), but the tremor disappears when the frequency is increased. See Constantoyannis 2004. Likewise, DBS of the subthalamic nucleus (STN) at 10 Hz worsens akinesia in patients with Parkinson's disease (PD), while DBS at 130 Hz leads to significant improvement in motor function See Timmermann et al. 2004, Fogelson et al. 2005. Similarly, stimulation of the globus pallidus (GP) at or above 130 Hz significantly improves dystonia, whereas stimulation at either 5 or 50 Hz leads to significant worsening. See Kupsch et al. 2003.

Model studies also indicate that the masking of pathological burst activity occurs only with sufficiently high stimulation frequencies. See Grill et al. 2004, FIG. 1. Responsiveness of tremor to changes in DBS amplitude and frequency are strongly correlated with the ability of applied stimuli to mask neuronal bursting. See Kuncel et al. 2007, FIG. 2.

Although effective, conventional high frequency stimulation generates stronger side-effects than low frequency stimulation, and the therapeutic window between the voltage that generates the desired clinical effect(s) and the voltage that generates undesired side effects decreases with increasing frequency. Precise lead placement therefore becomes important. Further, high stimulation frequencies increase power consumption. The need for higher frequencies and increased power consumption shortens the useful lifetime and/or increases the physical size of battery-powered implantable pulse generators. The need for higher frequencies and increased power consumption requires a larger battery size, and frequent charging of the battery, if the battery is rechargeable.

SUMMARY OF THE INVENTION

The invention provides stimulation patterns or trains with different temporal patterns of stimulation than conventional stimulation trains. The invention also provides methodologies to identify and characterize stimulation patterns or trains that produce desired relief of symptoms, while reducing the average stimulation frequency.

According to one aspect of the invention, the intervals between stimulation pulses in a pulse pattern or train (in shorthand called "the inter-pulse intervals") is not constant over time, but changes or varies over time. These patterns or trains are consequently called in shorthand "non-regular." According to this aspect of the invention, the non-regular (i.e., not constant) pulse patterns or trains provide a lower average frequency for a given pulse pattern or train, compared to conventional continuous, high rate pulse trains having regular (i.e., constant) inter-pulse intervals. Having a lower average frequency, the non-regular stimulus patterns or trains make possible an increase in the efficacy of stimulation by reducing the intensity of side effects; by increasing the dynamic range between the onset of the desired clinical effect(s) and side effects (and thereby reducing sensitivity to the position of the lead electrode); and by decreasing power consumption, thereby providing a longer useful battery life and/or a smaller implantable pulse generator, allowing battery size reduction and/or, for rechargeable batteries, longer intervals between recharging.

The non-regular stimulation patterns or trains can be readily applied to deep brain stimulation, to treat a variety of neurological disorders, such as Parkinson's disease, movement disorders, epilepsy, and psychiatric disorders such as obsessive-compulsion disorder and depression. The non-regular stimulation patterns or trains can also be readily applied to other classes electrical stimulation of the nervous system including, but not limited to, cortical stimulation, spinal cord stimulation, and peripheral nerve stimulation (including sensory and motor), to provide the attendant benefits described above and to treat diseases such as but not limited to Parkinson's Disease, Essential Tremor, Movement Disorders, Dystonia, Epilepsy, Pain, psychiatric disorders such as Obsessive Compulsive Disorder, Depression, and Tourette's Syndrome.

According to another aspect of the invention, systems and methodologies make it possible to determine the effects of the temporal pattern of DBS on simulated and measured neuronal activity, as well as motor symptoms in both animals and humans. The methodologies make possible the qualitative determination of the temporal features of stimulation trains.

The systems and methodologies described herein employ a genetic algorithm, coupled to a computational model of DBS of the STN, to develop non-regular patterns of stimulation that produced efficacy (as measured by a low error function, E) at lower stimulation frequencies, F. The error function, E, is a quantitative measure from the model which assesses how faithfully the thalamus transmitted motor commands that are generated by inputs from the cortex. A very high correlation exists between E and symptoms in persons with PD, and therefore E is a valid predictor for the efficacy of a stimulation train in relieving symptoms (see Dorval et al., 2007).

Previous efforts (see Feng et al. 2007) sought to design stimulation trains that minimized the total current injection. The systems and methodologies disclosed herein include an objective function that maximizes therapeutic benefit (by minimizing the error function) and improves stimulation efficiency (by reducing the stimulation frequency), using a model of the STN that reproduces the frequency tuning of symptom reduction that has been documented clinically. In contrast, the Feng et al. model showed, incorrectly, symptom reduction with regular, low frequency stimulation. The inventors have identified novel non-regular temporal patterns of stimulation, while Feng et al. identified regular low frequency (~10 Hz) trains that previous clinical work has demonstrated to be ineffective.

DESCRIPTION OF THE PREFERRED EMBODIMENTS

Figure 1:
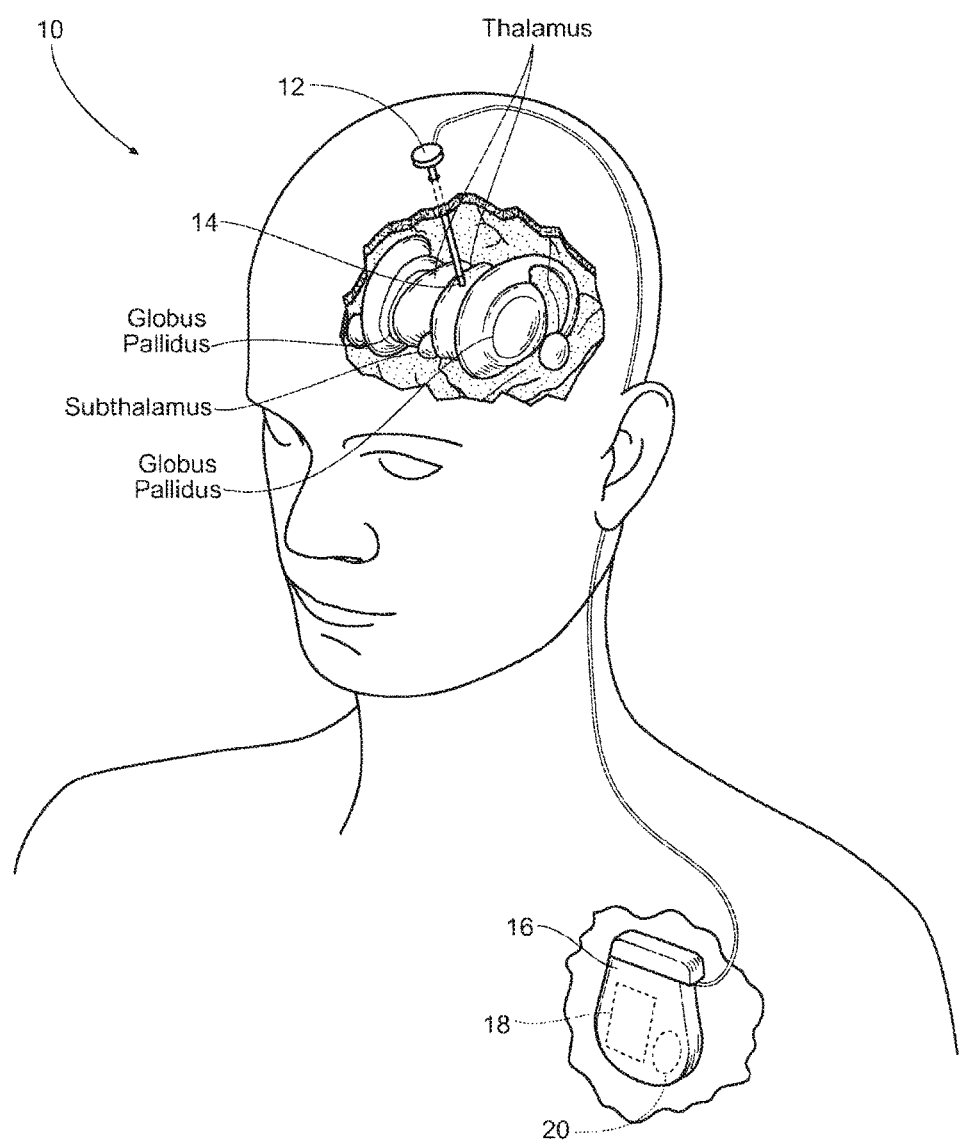
FIG. 1 is an anatomic view of a system for stimulating tissue of the central nervous system that includes an lead implanted in brain tissue coupled to a pulse generator that is programmed to provide non-regular (i.e., not constant) pulse patterns or trains, in which the interval between electrical pulses (the inter-pulse intervals) changes or varies over time.

FIG. 1 is a system 10 for stimulating tissue of the central nervous system. The system includes a lead 12 placed in a desired position in contact with central nervous system tissue. In the illustrated embodiment, the lead 12 is implanted in a region of the brain, such as the thalamus, subthalamus, or globus pallidus for the purpose of deep brain stimulation. However, it should be understood, the lead 12 could be implanted in, on, or near the spinal cord; or in, on, or near a peripheral nerve (sensory or motor) for the purpose of selective stimulation to achieve a therapeutic purpose.

The distal end of the lead 12 carries one or more electrodes 14 to apply electrical pulses to the targeted tissue region. The electrical pulses are supplied by a pulse generator 16 coupled to the lead 12.

In the illustrated embodiment, the pulse generator 16 is implanted in a suitable location remote from the lead 12, e.g., in the shoulder region. It should be appreciated, however, that the pulse generator 16 could be placed in other regions of the body or externally.

When implanted, the case of the pulse generator can serve as a reference or return electrode. Alternatively, the lead 12 can include a reference or return electrode (comprising a bi-polar arrangement), or a separate reference or return electrode can be implanted or attached elsewhere on the body (comprising a mono-polar arrangement).

The pulse generator 16 includes an on-board, programmable microprocessor 18, which carries embedded code. The code expresses pre-programmed rules or algorithms under which a desired electrical stimulation waveform pattern or train is generated and distributed to the electrode(s) 14 on the lead 12. According to these programmed rules, the pulse generator 16 directs the prescribed stimulation waveform patterns or trains through the lead 12 to the electrode(s) 14, which serve to selectively stimulate the targeted tissue region. The code is preprogrammed by a clinician to achieve the particular physiologic response desired.

In the illustrated embodiment, an on-board battery 20 supplies power to the microprocessor 18. Currently, batteries 20 must be replaced every 1 to 9 years, depending on the stimulation parameters needed to treat a disorder. When the battery life ends, the replacement of batteries requires another invasive surgical procedure to gain access to the implanted pulse generator. As will be described, the system 10 makes possible, among its several benefits, an increase in battery life.

Figure 2:
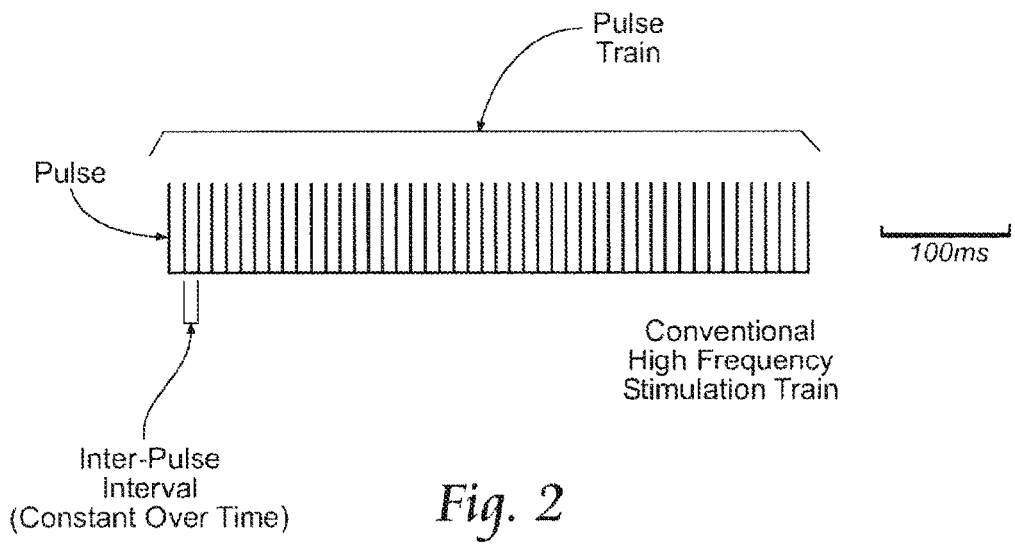
FIG. 2 is a diagrammatic trace that shows a conventional regular high frequency stimulation train, in which the interval between electrical pulses (the inter-pulse intervals) is constant.
Figure 3:
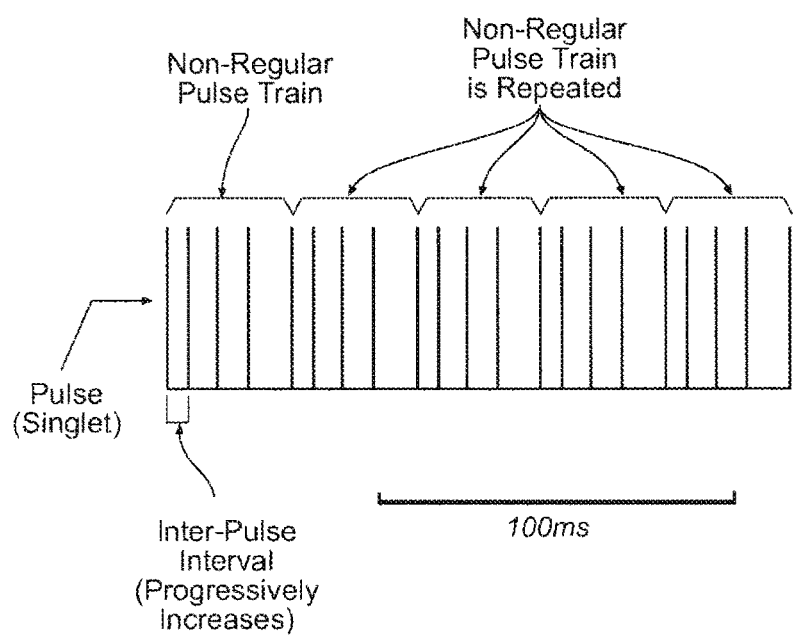
FIG. 3 is a diagrammatic trace showing a representative example of a repeating non-regular pulse pattern or train in which the inter-pulse intervals are linearly cyclically ramped over time.
Figure 4:
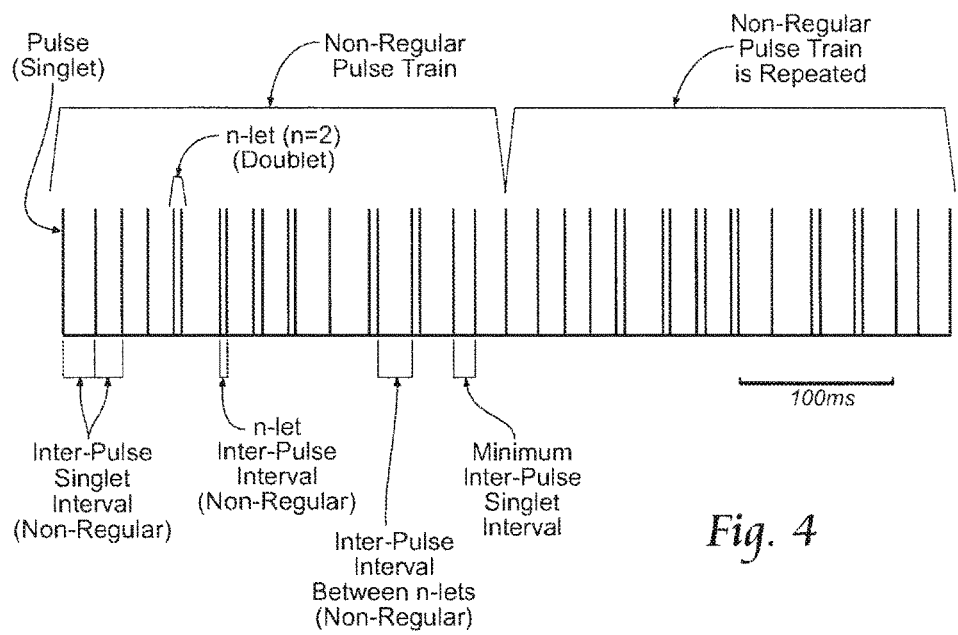
FIGS. 4 and 5 are diagrammatic traces showing other representative examples of repeating non-regular pulse patterns or trains comprising within, a single pulse train, a combination of single pulses (singlets) and embedded multiple pulse groups (n-lets), with non-regular inter-pulse intervals between singlets and n-lets as well as non-regular inter-pulse intervals within the multiple pulse n-lets.
Figure 5:
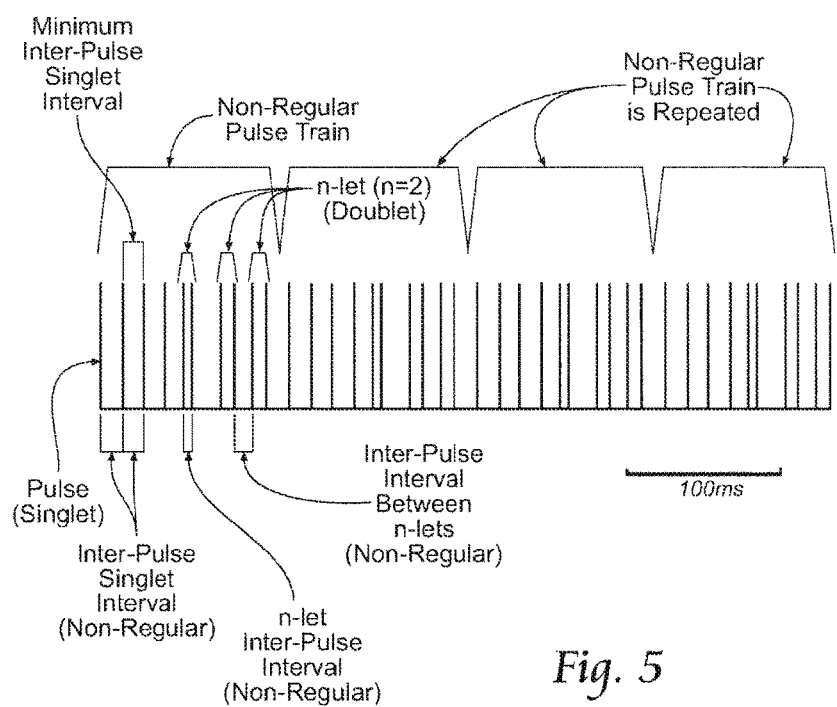

The stimulation waveform pattern or train generated by the pulse generator differs from convention pulse patterns or trains in that the waveform comprises repeating non-regular (i.e., not constant) pulse patterns or trains, in which the interval between electrical pulses (the inter-pulse intervals or IPI) changes or varies over time. Examples of these repeating non-regular pulse patterns or trains are shown in FIGS. 3 to 5. Compared to conventional pulse trains having regular (i.e., constant) inter-pulse intervals (as shown in FIG. 2), the non-regular (i.e., not constant) pulse patterns or trains provide a lower average frequency for a given pulse pattern or train, where the average frequency for a given pulse train (expressed in hertz or Hz) is defined as the sum of the inter-pulse intervals for the pulse train in seconds ($\Sigma_{IPI}$) divided by the number of pulses (n) in the given pulse train, or ($\Sigma_{IPI}$)/n. A lower average frequency makes possible a reduction in the intensity of side effects, as well as an increase in the dynamic range between the onset of the desired clinical effect(s) and side effects, thereby increasing the clinical efficacy and reducing sensitivity to the position of the electrode(s). A lower average frequency brought about by a non-regular pulse pattern or train also leads to a decrease in power consumption, thereby prolonging battery life and reducing battery size.

The repeating non-regular (i.e., not constant) pulse patterns or trains can take a variety of different forms. For example, as will be described in greater detail later, the inter-pulse intervals can be linearly cyclically ramped over time in non-regular temporal patterns (growing larger and/or smaller or a combination of each over time); or be periodically embedded in non-regular temporal patterns comprising clusters or groups of multiple pulses (called n-lets), wherein n is two or more. For example, when n=2, the n-let can be called a doublet; when n=3, the n-let can be called a triplet; when n=4, the n-let can be called a quadlet; and so on. The repeating non-regular pulse patterns or trains can comprise combinations of single pulses (called singlets) spaced apart by varying non-regular inter-pulse intervals and n-lets interspersed among the singlets, the n-lets themselves being spaced apart by varying non-regular inter-pulse intervals both between adjacent n-lets and between the n pulses embedded in the n-let. If desired, the non-regularity of the pulse pattern or train can be accompanied by concomitant changes in waveform and/or amplitude, and/or duration in each pulse pattern or train or in successive pulse patterns or trains.

Each pulse comprising a singlet or imbedded in an n-let in a given train comprises a waveform that can be monophasic, biphasic, or multiphasic. Each waveform possesses a given amplitude (expressed, e.g., in amperes) that can, by way of example, range from 10 μa ($E^{-6}$) to 10 ma ($E^{-3}$). The amplitude of a given phase in a waveform can be the same or differ among the phases. Each waveform also possesses a duration (expressed, e.g., in seconds) that can, by way of example, range from 10 μs ($E^{-6}$) to 2 ms ($E^{-3}$). The duration of the phases in a given waveform can likewise be the same or different. It is emphasized that all numerical values expressed herein are given by way of example only. They can be varied, increased or decreased, according to the clinical objectives.

When applied in deep brain stimulation, it is believed that repeating stimulation patterns or trains applied with non-regular inter-pulse intervals can regularize the output of disordered neuronal firing, to thereby prevent the generation and propagation of bursting activity with a lower average stimulation frequency than required with conventional constant frequency trains, i.e., with a lower average frequency than about 100 Hz.

FIG. 3 shows a representative example of a repeating non-regular pulse pattern or train in which the inter-pulse intervals are linearly cyclically ramped over time. As shown in FIG. 3, the pulse pattern or train includes singlet pulses (singlets) spaced apart by progressively increasing inter-pulse intervals providing a decrease in frequency over time, e.g., having an initial instantaneous frequency of 140 Hz, decreasing with doubling inter-pulse intervals, to a final instantaneous frequency of 40 Hz. The inter-pulse intervals can vary within a specified range selected based upon clinical objections, e.g., not to exceed 25 ms, or not to exceed 100 ms, or not to exceed 200 ms, to take into account burst responses and subsequent disruption of thalamic fidelity.). The non-regular pulse trains repeat themselves for a clinically appropriate period of time. As shown in FIG. 3, the first pulse train comprises progressively increasing inter-pulse intervals from smallest to largest, followed immediately by another essentially identical second pulse train comprising progressively increasing inter-pulse intervals from smallest to largest, followed immediately by an essentially identical third pulse train, and so on. Therefore, between successive pulse trains, there is an instantaneous change from the largest inter-pulse interval (at the end of one train) to the smallest inter-pulse interval (at the beginning of the next successive train). The train shown in FIG. 3 has an average frequency of 85 Hz and is highly non-regular, with a coefficient of variation (CV) of about 0.5. As is demonstrated in the following Example (Batch 3), the increased efficiency of the pulse train shown in FIG. 3 (due to the lower average frequency) also can provide greater efficacy, as compared to a constant 100 Hz pulse pattern.

The train shown in FIG. 3 exploits the dynamics of burst generation in thalamic neurons. The early high frequency phase of the train masks intrinsic activity in subthalamic nucleus (STN) neurons, and the inter-pulse interval increases reduce the average frequency. A family of trains can be provided by varying the initial frequency, final frequency, and rate of change within the train, with the objective to prevent thalamic bursting with a lower average stimulation frequency than required with constant frequency trains.

FIGS. 4 and 5 show other representative examples of repeating non-regular pulse patterns or trains. The pulse trains in FIGS. 4 and 5 comprise within, a single pulse train, a combination of single pulses (singlets) and embedded multiple pulse groups (n-lets), with non-regular inter-pulse intervals between singlets and n-lets, as well as non-regular inter-pulse intervals within the n-lets themselves. The non-regular pulse trains repeat themselves for a clinically appropriate period of time.

The non-regular pulse train can be characterized as comprising one or more singlets spaced apart by a minimum inter-pulse singlet interval and one or more n-lets comprising, for each n-let, two or more pulses spaced apart by an inter-pulse interval (called the "n-let inter-pulse interval") that is less than the minimum singlet inter-pulse interval. The n-let inter-pulse interval can itself vary within the train, as can the interval between successive n-lets or a successive n-lets and singlets. The non-regular pulse trains comprising singlets and n-lets repeat themselves for a clinically appropriate period of time.

In FIG. 4, each pulse train comprises four singlets in succession (with non-regular inter-pulse intervals there between); followed by four doublets in succession (with non-regular inter-doublet pulse intervals there between and non-regular inter-pulse intervals within each n-let); followed by a singlet, three doublets, and a singlet (with non-regular inter-pulse intervals there between and non-regular inter-pulse intervals within each n-let). The temporal pattern of this pulse train repeats itself in succession for a clinically appropriate period of time. The non-regular temporal pulse pattern shown in FIG. 4 has an average frequency of 67.82 Hz without loss of efficacy, as is demonstrated in the following Example, Batch 17.

In FIG. 5, each pulse train comprises four singlets in succession (with non-regular inter-pulse intervals there between); followed by three doublets in succession (with non-regular inter-doublet pulse intervals there between and non-regular inter-pulse intervals within each n-let). The temporal pattern of this pulse train repeats itself in succession for a clinically appropriate period of time. The non-regular temporal pulse pattern shown in FIG. 5 has an average frequency of 87.62 Hz without loss of efficacy, as is demonstrated in the following Example, Batch 18.

The following Example illustrates a representative methodology for developing and identifying candidate non-regular stimulation trains as shown in FIGS. 3 to 5 that achieve comparable or better efficacy at a lower average frequency (i.e., more efficiency) than constant inter-pulse interval trains.

EXAMPLE

Computational models of thalamic DBS (McIntyre et al. 2004, Birdno, 2009) and subthalamic DBS (Rubin and Terman, 2004) can be used with genetic-algorithm-based optimization (Davis, 1991) (GA) to design non-regular stimulation patterns or trains that produce desired relief of symptoms with a lower average stimulation frequency than regular, high-rate stimulation. McIntyre et al. 2004, Birdno, 2009; Rubin and Terman, 2004; and Davis, 1991 are incorporated herein by reference.

In the GA implementation, the stimulus train (pattern) is the chromosome of the organism, and each gene in the chromosome is the IPI between two successive pulses in the train. The implementation can start, e.g., with trains of 21 pulses (20 genes) yielding a train length of ~400 ms (at average frequency of 50 Hz), and the 6 s trains required for stimulation are built by serial concatenation of 15 identical pulse trains. The process can start with an initial population of, e.g., 50 organisms, constituted of random IPI's drawn from a uniform distribution. At each step (generation) of the GA, the fitness of each pulse train is evaluated using either the TC or basal ganglia network model (identified above) and calculating a cost function, C. From each generation, the 10 best stimulus trains (lowest C) are selected, to be carried forward to the next generation. They will also be combined (mated) and random variations (mutations) introduced into the 40 offspring, yielding 50 trains in each generation. This process assures that the best stimulation trains (traits) are carried through to the next generation, while avoiding local minima (i.e., mating and mutations preserve genetic diversity). See Grefenstette 1986. The GA continues through successive generations until the median and minimum values of the cost function reach a plateau, and this will yield candidate trains.

The objective is to find patterns of non-constant inter-pulse interval deep brain stimulation trains that provide advantageous results, as defined by low frequency and low error rate. An error function is desirably created that assigns the output of each temporal pattern of stimulation a specific error fraction (E) based on how the voltage output of the thalamic cells correspond to the timing of the input stimulus. Using this error fraction, a cost function (C) is desirably created to minimize both frequency and error fraction, according to representative equation $C=W*E+K*f$, where C is the cost, E is the error fraction, f is the average frequency of the temporal pattern of stimulation, W is an appropriate weighting factor for the error function, and K is an appropriate weighting factor for the frequency. The weighting factors W and K allow quantitative differentiation between efficacy (E) and efficiency (f) to generate patterns of non-constant inter-pulse interval deep brain stimulation trains that provide advantageous results with lower average frequencies, compared to conventional constant frequency pulse trains.

With this cost function, the voltage output of several candidate temporal patterns of stimulation can be evaluated and the cost calculated. Temporal patterns of stimulation with a low cost can then be used to create new temporal patterns of similar features in an attempt to achieve even lower costs. In this way, new temporal patterns of stimulation can be "bred" for a set number of generations and the best temporal patterns of stimulation of each batch recorded.

Several batches of the genetic algorithm yields useful results in that they achieve lower costs than the corresponding constant frequency DBS waveforms. Some batches can be run in an attempt to find especially low frequency temporal patterns of stimulation, by changing the cost function to weight frequency more heavily, or vice versa (i.e., by changing W and/or K). These batches can also yield lower cost results than the constant-frequency waveforms.

By way of example, a total of 14 batches of the genetic algorithm were run and evaluated with various cost functions and modified initial parameters.

Figure 6:
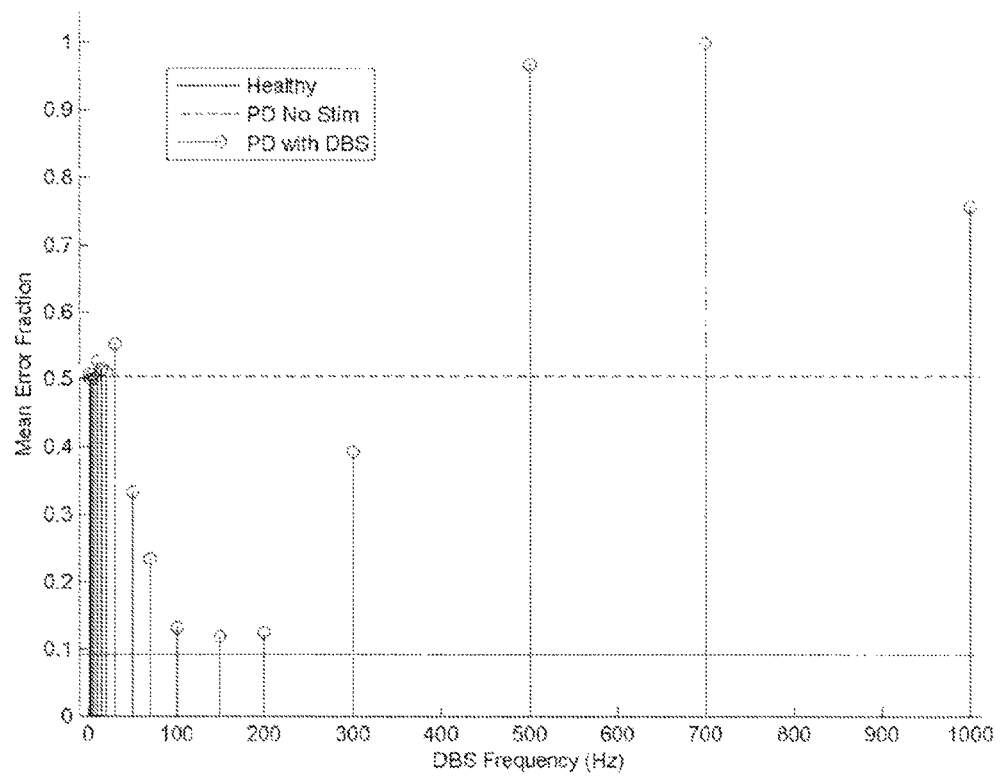
FIG. 6 is a graph plotting error fractions (E) for a range of constant-frequency deep brain stimulation patterns generated by a genetic algorithm model, used as a baseline for comparison with later non-constant temporal patterns developed in later batches of the genetic algorithm.

Before the trials were run, a baseline was established by running constant-frequency patterns of stimulation through the model and analyzing the associated error fractions (FIG. 6). As can be seen from FIG. 6, the healthy condition produced a low error fraction of 0.1 while the Parkinsonian condition without DBS yielded a higher error fraction of 0.5. From these results, constant high-frequency patterns of stimulation ranging from 100-200 Hz gave near perfect results. Novel non-constant temporal patterns of stimulation would then be considered advantageous if they showed error fractions very close to 0.1 with average frequencies less than 100-200 Hz.

Figure 7:
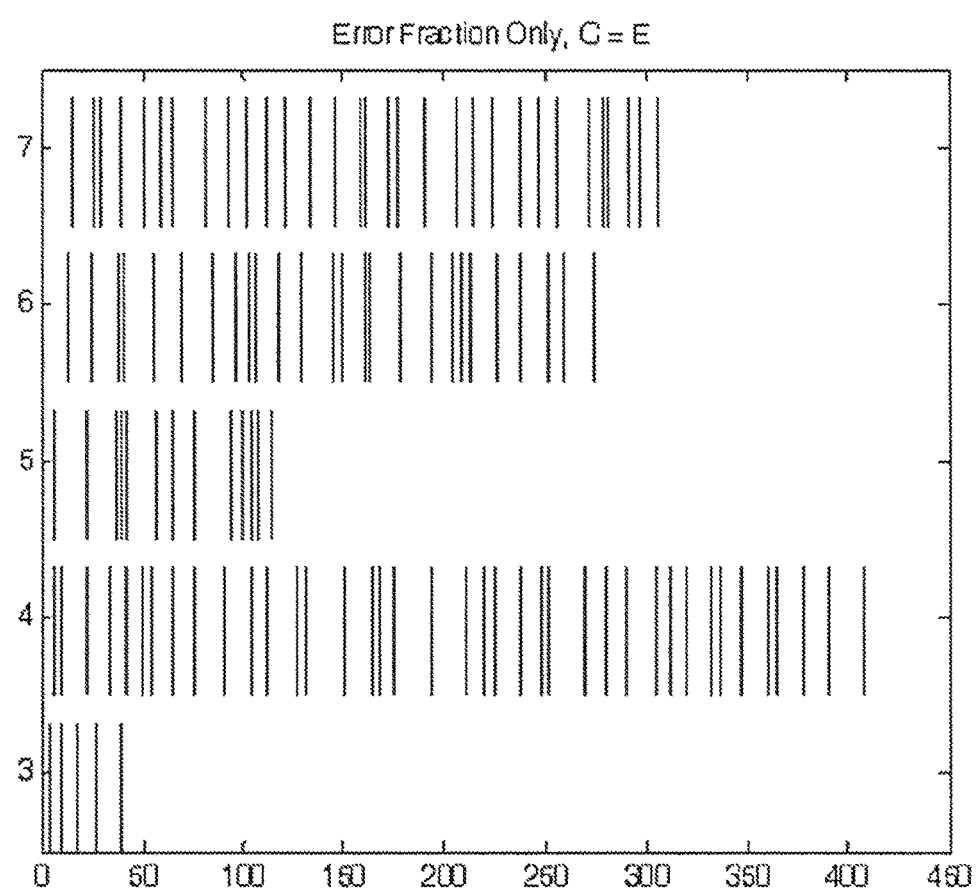
FIG. 7 is a plot of inter-pulse intervals (IPI's) of a first generational set of Batches 3 to 7 run through the genetic algorithm model in which the Cost Function (C) minimized only the error fractions (Cost Function C=E).

The first set of batches was run by minimizing only the error fraction (E). Thus, the associated cost function was simply C=E. The results are summarized according to average frequency and error fraction (Example Table 1). The associated inter-pulse intervals (IPI's) can be seen in FIG. 7. Batch 3 outputted an error fraction 0.054. Another interesting feature is that the IPI's in Batch 3 gradually increased until about 40 msec, and then repeated itself. This provides support that ramp trains are advantageous. The trace shown in FIG. 3 generally incorporates the temporal features of Batch 3.

The remaining batches yielded error fractions higher than 0.1 and were no better than the 150 Hz constant-frequency case.

EXAMPLE TABLE 1

Error Fraction Only, C = E

| # | Average Frequency | Error Fraction | IPI Length |
|---|---|---|---|
| 3 | 127.5 | 0.054 | 5 |
| 4 | 95.62 | 0.162 | 39 |
| 5 | 113.6 | 0.139 | 13 |
| 6 | 94.64 | 0.132 | 26 |
| 7 | 101.6 | 0.142 | 31 |

Because many batches were yielding error fractions above 0.1 (healthy condition), and only a small window of error fraction less than the 150 Hz DBS case would be useful, a new cost function was constructed to minimize an alternate feature of the temporal patterns of stimulation; namely, frequency. This new cost function weighted the error fraction and frequency, yielding the equation $C=1000*E+F$, where C is cost, E is error fraction, and F is the average frequency of the waveform in Hz, W=1000, and K=1.

Figure 8:
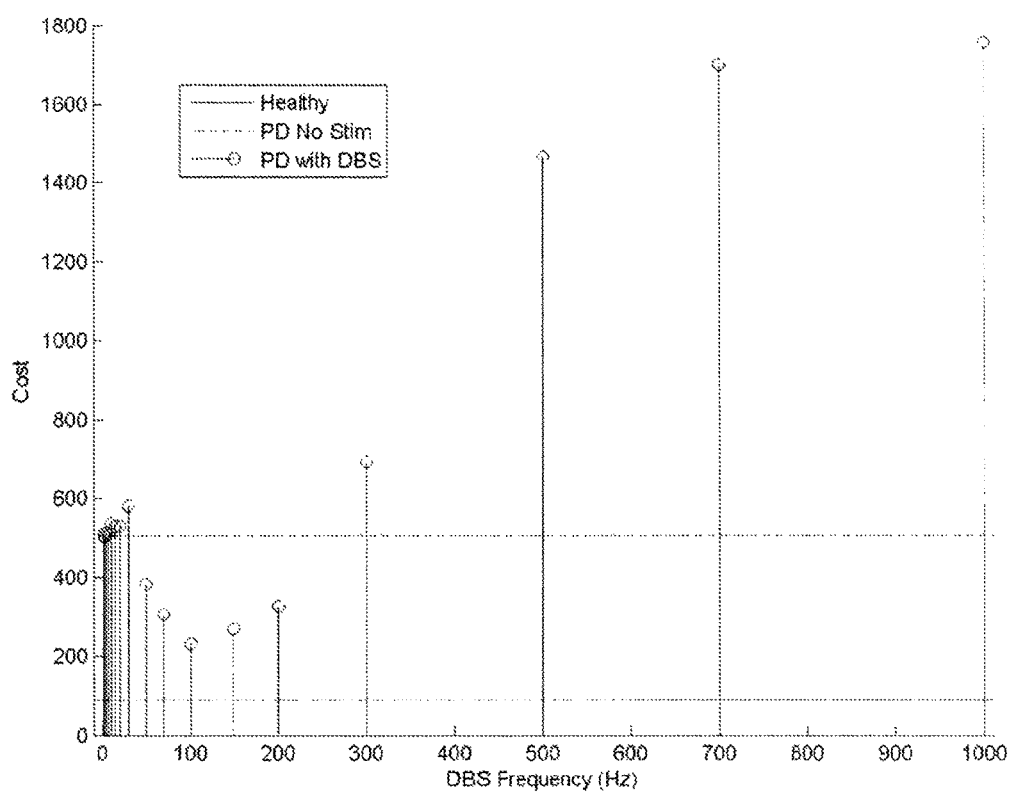
FIG. 8 is a graph plotting a new Cost Function C that weighted the error fraction (E) and average frequency (F) (C=1000*E+F) for the range of constant-frequency deep brain stimulation patterns used in FIG. 6, to establish a new baseline cost for comparison with later non-constant temporal patterns developed in later batches of the genetic algorithm.

In order to establish a new baseline cost, the constant-frequency patterns of stimulation were evaluated again according to the new cost function (FIG. 8). As can be seen from the graph, the healthy condition reported a cost of 90.65 and the Parkinson case with no DBS yielded 505.50. The best constant-frequency pattern of stimulation with the new cost function was the 100 Hz case with a cost of 231.11. This new cost' function allowed for a wider range of solutions, because a temporal pattern of stimulation would be considered useful if it had a cost less than 231.11 but presumably higher than 90.65.

Figure 9:
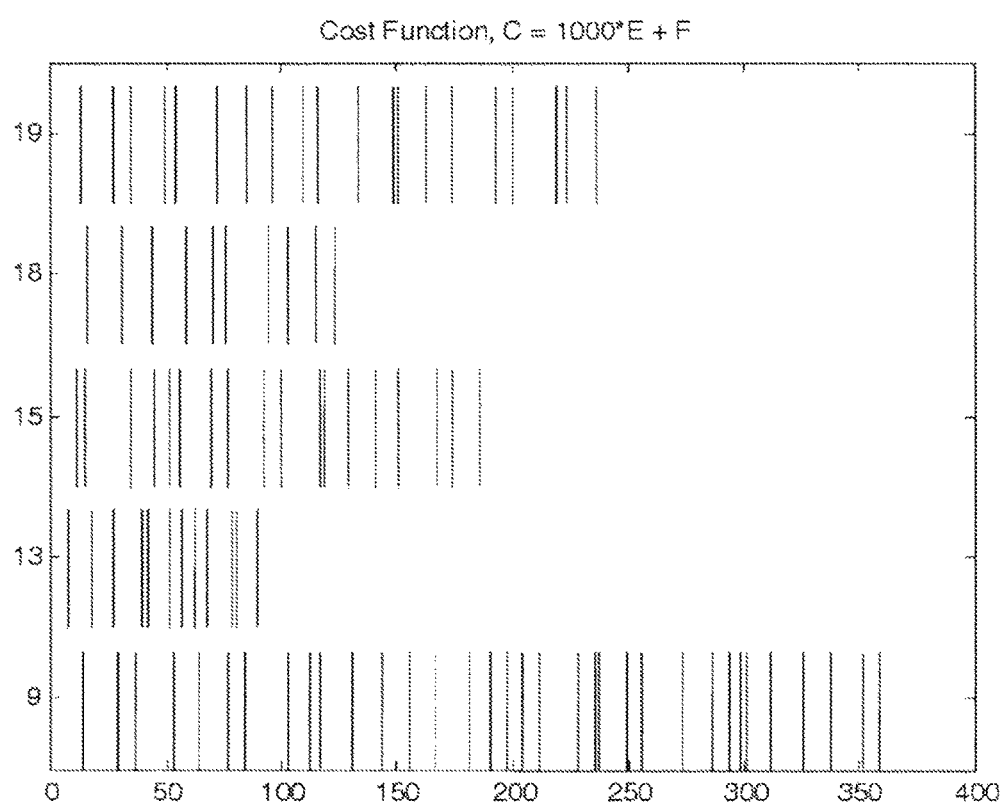
FIG. 9 is a plot of inter-pulse intervals (IPI's) of a next generational set of Batches 9, 13, 15, 18, and 19 run through the genetic algorithm model in which the Cost Function (C) weighted the error fraction (E) and average frequency (F) (C=1000*E+F).

The results of the new cost function can be seen in Example Table 2 and the IPI's visualized in FIG. 9. The best results were seen in batches 15 and 18, which had the lowest costs. Batch 18 is interesting in that it also exhibits a ramp-like pattern of increasing interpulse intervals. It shows a steadily falling IPI, followed by a sudden rise, and then a quick fall, rise, and fall-almost as if it consists of 3 smaller ramps. The trace shown in FIG. 5 generally incorporates the temporal features of Batch 18. Batch 15 also performed very well, but its qualitative features are more difficult to discern.

EXAMPLE TABLE 2

| | | Cost Function, C = 1000 * E + F | | |
|---|---|---|---|---|
| # | Average Frequency | IPI Length | Error Fraction | Cost |
| 9 | 94.74 | 34 | 0.124 | 218.8 |
| 13 | 132.9 | 12 | 0.087 | 219.4 |
| 15 | 98.00 | 17 | 0.098 | 196.0 |
| 18 | 81.28 | 10 | 0.116 | 197.3 |
| 19 | 84.70 | 20 | 0.116 | 201.2 |

The advantage of low frequency was emphasized with a new cost function, which weighted frequency more heavily, C=1000*E+2*F. Because the frequency of DBS does not affect the healthy condition or the PD with no DBS, these baseline costs stayed the same at 90.65 and 505.50, respectively. The 100 Hz was again the best constant-frequency temporal pattern of stimulation, with a cost of 331.11. The following temporal patterns of stimulation, then, were considered useful if they had low frequencies and costs less than 331.11 and greater than 90.65.

Figure 10:
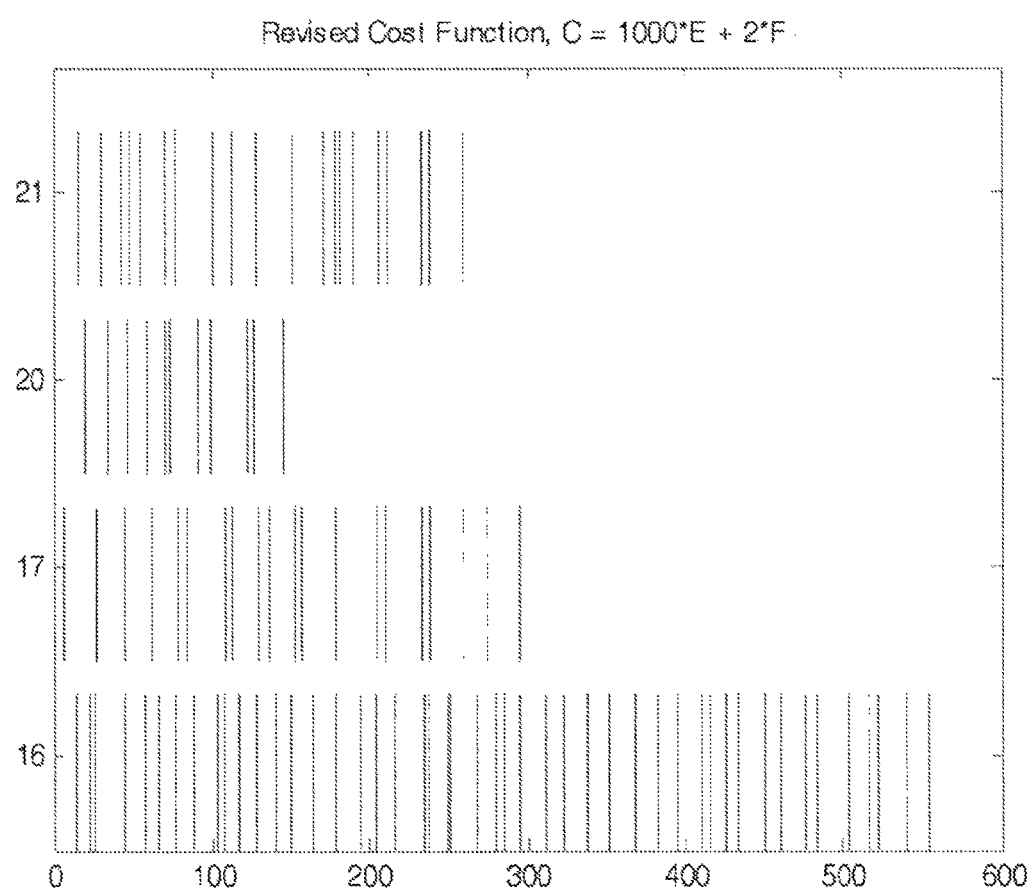
FIG. 10 is a plot of inter-pulse intervals (IPI's) of a further generational set of Batches 16, 17, 20, and 21 run through the genetic algorithm model in which a new Cost Function (C) weighted the average frequency more heavily than in FIG. 9 (C=1000*E+2*F).

The results of the revised cost function can be seen in Example Table 3 and the IPI's visualized in FIG. 10. Of the resulting batches, batch 17 proved most interesting because of its very low average frequency of 67.82 Hz. Even with such a low frequency, it managed to prove better than the 100 Hz condition with a reduction in cost of about 10. The waveform of batch 17 is interesting in that it consists of a ramp pattern of decreasing IPI in the first 100 msec, followed by continual shift between large IPI and small IPI. The qualitative feature of quickly changing between large and small IPI's may prove advantageous. The trace shown in FIG. 4 generally incorporates the temporal features of Batch 17.

EXAMPLE TABLE 3

| | | Revised Cost Function, Cost = 1000 * E + 2 * F | | |
|---|---|---|---|---|
| # | Average Frequency | IPI Length | Error Fraction | Cost |
| 16 | 84.92 | 47 | 0.239 | 323.8 |
| 17 | 67.82 | 20 | 0.253 | 321.1 |

EXAMPLE TABLE 3-continued

| | | Revised Cost Function, Cost = 1000 * E + 2 * F | | |
|---|---|---|---|---|
| # | Average Frequency | IPI Length | Error Fraction | Cost |
| 20 | 79.25 | 10 | 0.236 | 315.4 |
| 21 | 77.15 | 20 | 0.269 | 346.6 |

The most interesting temporal patterns of stimulation in this Example are from batches 15, 17, and 18. Batch 15 produced a temporal pattern of stimulation with an average frequency of 98 Hz with an error fraction as low as 0.098. Thus, it outperformed the 100 Hz constant-frequency case by managing to lower the error even further at roughly the same frequency. Still, the qualitatively useful features of batch 15 are difficult to discern. Batch 17 was also appealing because of its very low frequency of 67.82. This low frequency was gained at the cost of increased error at 0.253, but it may nonetheless be useful if emphasis is placed on maintaining low frequency DBS. The qualitative features of batch 17 indicated at first a ramp followed by a continual switching between low and high IPI's. Lastly, batch 18 stood somewhere in the middle with a fairly low frequency of 87.62 and low error fraction of 0.116, only marginally higher than the healthy condition of 0.1. The dominant qualitative feature of batch 18's waveform is that it too shows a ramp nature in that the IPI initially steadily falls, then quickly rises, falls, and then rises. The rapid changing between high and low IPI of batch 17 can be envisioned as a set of steep ramps.

A comparison of Batch 17 (FIG. 4) and Batch 18 (FIG. 5) demonstrates how the balance between efficacy (E) and efficiency (f) in non-regular temporal patterns of stimulation can be purposefully tailored to meet clinical objectives. The systems and methodologies discussed allow changing the cost function by weighting efficacy (E) or frequency (f) more heavily (i.e., by changing W and/or K), while still yielding temporal patterns of stimulation with lower cost results than the constant-frequency waveforms. Comparing Batch 17 with Batch 18, one sees that the error fraction (E) (i.e., the efficacy of the temporal pattern) of Batch 17 (0.253) is greater than the error fraction (E) (i.e., the efficacy of the temporal pattern) of Batch 18 (0.116). However, one can also see that the efficiency (i.e., the average frequency) of Batch 17 (67.82 Hz) is lower than the efficiency (i.e., the average frequency) of Batch 18 (81.28 Hz). Through different in terms of efficacy and efficiency, both Batch 17 and Batch 18 have costs better than constant-frequency temporal patterns.

The non-regular temporal patterns of stimulation generated and disclosed above therefore make possible achieving at least the same or equivalent (and expectedly better) clinical efficacy at a lower average frequency compared to conventional constant-frequency temporal patterns. The lower average frequencies of the non-regular temporal stimulation patterns make possible increases in efficiency and expand the therapeutic window of amplitudes that can be applied to achieve the desired result before side effects are encountered.

DBS is a well-established therapy for treatment of movement disorders, but the lack of understanding of mechanisms of action has limited full development and optimization of this treatment. Previous studies have focused on DBS-induced increases or decreases in neuronal firing rates in the basal ganglia and thalamus. However, recent data suggest that changes in neuronal firing patterns may be at least as important as changes in firing rates.

The above described systems and methodologies make it possible to determine the effects of the temporal pattern of DBS on simulated and measured neuronal activity, as well as motor symptoms in both animals and humans. The methodologies make possible the qualitative and quantitative determination of the temporal features of low frequency stimulation trains that preserve efficacy.

The systems and methodologies described herein provide robust insight into the effects of the temporal patterns of DBS, and thereby illuminate the mechanisms of action. Exploiting this understanding, new temporal patterns of stimulation can be developed, using model-based optimization, and tested, with the objective and expectation to increase DBS' efficacy and increase DBS efficiency by reducing DBS side effects.

The invention provides non-regular stimulation patterns or trains that can create a range of motor effects from exacerbation of symptoms to relief of symptoms. The non-regular stimulation patterns or trains described herein and their testing according to the methodology described herein will facilitate the selection of optimal surgical targets as well as treatments for new disorders. The non-regular stimulation patterns or trains described herein make possible improved outcomes of DBS by reducing side effects and prolonging battery life.

LITERATURE CITATIONS

Benabid A L, Pollak P, Gervason C, Hoffmann D, Gao D M, Hommel M, Perret J E, de Rougemont J (1991) Long-term suppression of tremor by chronic stimulation of the ventral intermediate thalamic nucleus. Lancet. 337:403-6.

Birdno M J "Analyzing the mechanisms of thalamic deep brain stimulation: computational and clinical studies". Ph.D. Dissertation. Department of Biomedical Engineering, Duke University, Durham, N.C., USA, August 2009.

Constantoyannis C, Kumar A, Stoessl A J, Honey C R (2004) Tremor induced by thalamic deep brain stimulation in patients with complex regional facial pain. Mov Disord. 19:933-936.

Davis L (1991) Handbook of genetic algorithms. Van Nostrand Reinhold, N.Y.

Dorval A D, Kuncel A M, Birdno M J, Turner D A, Grill W M (2007) Deep brain stimulation alleviates Parkinsonian bradykinesia by regularizing thalamic throughput in human subjects. Society for Neuroscience Abstracts 32.

Feng X J, Shea-Brown E, Greenwald B, Kosut R, Rabitz H (2007) Optimal deep brain stimulation of the subthalamic nucleus-a computational study. J Comput Neurosci. 23(3):265-282.

Fogelson N, Kuhn A A, Silberstein P, Limousin P D, Hariz M, Trottenberg T, Kupsch A, Brown P (2005) Frequency dependent effects of subthalamic nucleus stimulation in Parkinson's disease. Neuroscience Letters 382:5-9.

Grefenstette J J (1986) Optimization of Control Parameters for Genetic Algorithms. IEEE Transactions on Systems, Man and Cybernetics 16:122-128.

Grill W M, Cooper S E, Montgomery E B (2003) Effect of stimulus waveform on tremor suppression and paresthesias evoked by thalamic deep brain stimulation. Society for Neuroscience Abstracts 29.

Kuncel A M, Cooper S E, Montgomery E B, Baker K B, Rezai A R, Grill W M (2006) Clinical response to varying the stimulus parameters in deep brain stimulation for essential tremor. Movement Disorders 21(11):1920-1928.

Kupsch A, Klaffke S, Kuhn A A, Meissner W, Arnold G, Schneider G H, Maier-Hauff K, Trottenberg T (2003) The effects of frequency in pallidal deep brain stimulation for primary dystonia. J Neurol 250:1201-1204.

Limousin P, Pollack P, Benazzouz A (1995) Effect on Parkinsonian signs and symptoms of bilateral stimulation. The Lancet 345:91-95.

McIntyre C C, Grill W M, Sherman D L, Thakor N V (2004) Cellular effects of deep brain stimulation: model-based analysis of activation and inhibition. J Neurophysiol 91:1457-1469.

Rubin J E, Terman D (2004) High frequency stimulation of the subthalamic nucleus eliminates pathological thalamic rhythmicity in a computational model. J Comput Neurosci 16:211-235.

Timmermann L, Gross J, Dirks M, Volkmann J, Freund H J, Schnitzler A (2003) The cerebral oscillatory network of parkinsonian resting tremor. Brain, 126:199-212.

Having thus described the invention, the following is claimed:

1. A method comprising the steps of:
   applying electrical current to targeted neurological tissue region of a brain using an implantable pulse generator system including an electrode and a lead, wherein the pulse generator applies a non-regular pulse train comprising a plurality of pulses having non-regular, non-random, differing inter-pulse intervals therebetween;
   wherein the inter-pulse intervals are linearly cyclically ramped over time; and wherein optionally, an amplitude of at least one of the pulses is different from a second pulse amplitude of another of the pulses of the non-regular pulse train, and
   repeating the applying step in succession at least once to treat a neurological condition.

2. The method of claim 1, wherein the neurological condition is one of Parkinson's Disease, Essential Tremor, Movement Disorders, Dystonia, Epilepsy, Pain, Obsessive Compulsive Disorder, Depression and Tourette's Syndrome.

3. The method of claim 1, wherein a waveform shape of at least one of the pulses is different from a second pulse waveform shape of another of the pulses of the non-regular pulse train.

4. The method of claim 1, wherein each pulse of the plurality of pulses comprises a waveform that is either of monophasic, biphasic, or multiphasic.

5. The method of claim 1, wherein at least one of the pulses comprises a monophasic waveform.

6. The method of claim 1, wherein at least one of the pulses comprises a biphasic waveform.

7. The method of claim 1, wherein at least one of the pulses comprises a multiphasic waveform.

8. A system for neurological tissue stimulation comprising an electrode sized and configured for implantation in the targeted tissue stimulation region of the brain, and
   an implantable pulse generator coupled to the electrode, the pulse generator operable to apply a temporal pattern of stimulation to the targeted tissue through the electrode comprising the non-regular pulse train configured as defined in claim 1.

9. A medical stimulation system comprising;
   an implantable pulse generator operatively coupled with an electrode by way of a lead; and
   the pulse generator configured to transmit an electrical signal to a neurological tissue region of a brain, the electrical signal comprising a repeating succession of non-regular pulse trains, each pulse train comprising a plurality of pulses with non-regular, non-random, differing inter-pulse intervals therebetween;
wherein the inter-pulse intervals are linearly cyclically ramped over time; and
optionally, wherein an amplitude of at least one of the pulses is different from a second pulse amplitude of another of the pulses of the non-regular pulse train, whereby the pulse train treats a neurological symptom.

10. The medical stimulation system of claim 9, further comprising a lead operatively coupled between the electrode and the pulse generator.

11. The medical stimulation system of claim 9, wherein the pulse generator is pre-programmed to contain the non-regular pulse train.

12. The medical stimulation system of claim 9, wherein the pulse generator includes a programmable microprocessor.

13. A method comprising the steps of:
applying electrical current to targeted neurological tissue region of a brain using an implantable pulse generator system including a lead, wherein the pulse generator applies a non-regular pulse train comprising a plurality of pulses having non-regular, non-random, differing inter-pulse intervals therebetween and wherein the inter-pulse intervals are linearly cyclically ramped over time, and
repeating the applying step in succession to achieve a therapeutic purpose.

14. The method of claim 13, wherein the therapeutic purpose is to treat a neurological condition.

15. The method of claim 14, wherein the neurological condition is one of Parkinson's Disease, Essential Tremor, Movement Disorders, Dystonia, Epilepsy, Pain, Obsessive Compulsive Disorder, Depression and Tourette's Syndrome.

16. The method of claim 13, wherein a waveform shape of at least one of the pulses is different from a second pulse waveform shape of another of the pulses of the non-regular pulse train.

17. The method of claim 13, wherein each pulse of the plurality of pulses comprises a waveform that is either of monophasic, biphasic, or multiphasic.

18. The method of claim 13, wherein at least one of the pulses comprises a monophasic waveform.

19. The method of claim 13, wherein at least one of the pulses comprises a biphasic waveform.

20. The method of claim 13, wherein at least one of the pulses comprises a multiphasic waveform.

21. A method comprising the steps of:
applying electrical current to targeted neurological tissue region of a brain of a patient through at least one electrode operatively coupled with an implanted pulse generator by way of at least one lead, the pulse generator applying a non-regular pulse train comprising a plurality of pulses having non-regular, non-random, differing inter-pulse intervals therebetween;
wherein the inter-pulse intervals are linearly cyclically ramped over time and wherein an amplitude of at least one of the pulses is different from a second pulse amplitude of another of the pulses of the non-regular pulse train, and
repeating the applying step in succession to modify a state of a patient.

22. A method comprising the steps of:
applying electrical current to targeted neurological tissue region of a brain using an implantable pulse generator, wherein the implantable pulse generator is operatively coupled with an electrode via a lead for delivering a non-regular pulse train comprising a plurality of pulses having non-regular, non-random, differing inter-pulse intervals therebetween and wherein the inter-pulse intervals are linearly cyclically ramped over time and wherein, optionally, an amplitude of at least one of the pulses is different from a second pulse amplitude of another of the pulses of the non-regular pulse train, and
repeating the applying step in succession at least once to achieve a desired physiological response.

23. A medical stimulation system comprising;
an implantable pulse generator operatively coupled with an electrode by way of a lead;
the pulse generator configured to transmit an electrical signal to a neurological tissue of a brain, the electrical signal comprising a repeating succession of non-regular pulse trains, each pulse train comprising a plurality of pulses having non-regular, non-random, differing inter-pulse intervals therebetween and wherein the inter-pulse intervals are linearly cyclically ramped over time and wherein an amplitude of at least one of the pulses is different from a second pulse amplitude of another of the pulses of the non-regular pulse train, whereby the pulse train modifies a state of a patient.

24. A medical stimulation system comprising;
an implantable pulse generator operatively coupled with an electrode by way of a lead;
the pulse generator configured to transmit an electrical signal to a neurological tissue of a brain, the electrical signal comprising a repeating succession of non-regular pulse trains, each pulse train comprising a plurality of pulses having non-regular, non-random, differing inter-pulse intervals therebetween and wherein the inter-pulse intervals are linearly cyclically ramped over time and, the pulse train repeating in succession at least once to achieve a desired physiological response.

25. A medical stimulation system comprising;
an implantable pulse generator operatively coupled with an electrode by way of a lead;
a programmable microprocessor coupled with the pulse generator; and
embedded code stored on the programmable microprocessor;
wherein the embedded code expresses programmed rules under which an electrical signal is applied through the electrode to a neurological tissue of a brain, whereby the electrical signal comprises a repeating succession of non-regular pulse trains, each pulse train comprising a plurality of pulses having non-regular, non-random, differing inter-pulse intervals therebetween and wherein the inter-pulse intervals are linearly cyclically ramped over time.

26. The medical stimulation system of claim 25, wherein the pulse train repeats in succession to achieve a desired physiological response.

27. The medical stimulation system of claim 25, wherein the embedded code is programmed to achieve a desired physiological response.

28. The medical stimulation system of claim 25, wherein an amplitude of at least one of the pulses is different from a second pulse amplitude of another of the pulses of the non-regular pulse train.

* * * * *